United States Patent
Pizanias (10) Patent No.: US 10,716,567 B2
(45) Date of Patent: Jul. 21, 2020

(54) WOUND CLOSURE SYSTEM

(71) Applicant: Vlassios Pizanias, Campbell, OH (US)

(72) Inventor: Vlassios Pizanias, Campbell, OH (US)

(*) Notice: Subject to any disclaimer, the term of this patent is extended or adjusted under 35 U.S.C. 154(b) by 203 days.

(21) Appl. No.: 15/976,132

(22) Filed: May 10, 2018

(65) Prior Publication Data

US 2018/0325520 A1    Nov. 15, 2018

Related U.S. Application Data

(60) Provisional application No. 62/504,020, filed on May 10, 2017.

(51) Int. Cl.
*A61B 17/08* (2006.01)

(52) U.S. Cl.
CPC ...... *A61B 17/085* (2013.01); *A61B 2017/086* (2013.01)

(58) Field of Classification Search
CPC ............ A61B 17/085; A61B 2017/086; A61B 2017/088; A61B 17/08; A61B 2017/081
See application file for complete search history.

(56) References Cited

U.S. PATENT DOCUMENTS

| | | | |
|---|---|---|---|
| 2,387,131 A | 10/1945 | Fernandez | |
| 3,971,384 A | 7/1976 | Hasson | |
| 4,825,866 A | 5/1989 | Pierce | |
| 5,843,123 A * | 12/1998 | Brazeau | A61B 17/085 606/213 |
| 8,157,839 B2 | 4/2012 | Riskin et al. | |
| 9,050,086 B2 | 6/2015 | Belson et al. | |
| 2003/0092969 A1 | 5/2003 | O'Malley et al. | |
| 2009/0149869 A1 | 6/2009 | Dolhun | |
| 2011/0282260 A1 | 11/2011 | Kim et al. | |

FOREIGN PATENT DOCUMENTS

WO    2017023901 A1    2/2017

* cited by examiner

*Primary Examiner* — Katrina M Stransky
(74) *Attorney, Agent, or Firm* — Jacob M. Ward; Ward Law Office LLC (57) ABSTRACT

A wound closure system includes a device having a first main body and a second main body. Each of the first main body and the second main body has an adhesive backing. The first main body is coupled to the second main body by an adjustable connector. The adjustable connector is permitted to move in a single direction. In the event of an injury, the first and second main bodies are placed on opposite sides of a wound and are then pulled together, thereby sealing the wound.

11 Claims, 7 Drawing Sheets

WOUND CLOSURE SYSTEM

CROSS-REFERENCE TO RELATED APPLICATIONS

This application claims the benefit of U.S. Provisional Application No. 62/504,020, filed on May 10, 2017. The entire disclosure of the above application is hereby incorporated herein by reference.

FIELD

The present disclosure relates to a wound closure system and, more particularly, to adjustable devices for closing wounds.

BACKGROUND

Closure of wounds such as cuts have traditionally involved stitches or staples. The technique of properly stitching a wound takes years to perfect. Unfortunately, the average person does not know how to properly stitch a wound in an emergency. Moreover, stitches and staples are not adjustable. If the wound becomes inflamed, the stitches can break and the wound will rupture.

Furthermore, surgeons confronted with suturing a morbidly obese patient using retention sutures can subject the patient to complications such as intense pain and pulling at the wound site.

There are a multitude of other devices known for closing wounds. These known devices close and secure a wound, stop or prevent bleeding, and can minimize the possibility of secondary infections. Such devices include adhesive bandages or butterfly bandages. However, these adhesive bandages are generally suitable for only minor cuts and scrapes, are prone to accidental removal, and are typically not suitable for closing major wounds.

Another known wound closure device is described in U.S. Pat. No. 9,050,086 to Belson et al. In particular, Belson et al. discloses an apparatus for closing a surgical incision, which comprises a plurality of closure components for coupling left and right base panels to each other laterally. A plurality of left and right axial supports are coupled to the respective base panels. As these panels are pushed closer, the panels interlock to thereby close a wound.

There is a continuing need for a wound closure system that can be used with minimal training for both minor and major wounds. Desirably, the wound closure system can be securely attached to the patient, and is rapidly adjustable so as to close wounds quickly and cleanly.

SUMMARY

In concordance with the instant disclosure, a wound closure system that can be used with minimal training for both minor and major wounds, and which can be securely attached to the patient, and is rapidly adjustable so as to close wounds quickly and cleanly, has been surprisingly discovered.

In one embodiment, a wound closure system has a first main body and a second main body. Each of the first main body and the second main body has an adhesive backing. The first main body is linked to the second main body by an adjustable connector. The first and second main bodies are attached to the adjustable connector at an angled wall. The wall is angled to create a force downward when there is tension between the first main body and second main body, which helps keep the main bodies attached to a patient's body. The adjustable connector includes or is connected with a closure mechanism that only allows movement of the adjustable connector in one direction. Thus, when the adjustable connector is pulled, it draws the first and second main body together, militating against any rearward movement. In operation, this is effective in closing a wound.

Within the scope of the present disclosure, a variety of adjustable connectors are contemplated. The adjustable connector can be a cord or rope tied in a knot that only allows movement in a single direction. The adjustable connector can also be a cord or rope that is linked to a unidirectional structure, including a body having an aperture with teeth, the teeth interlocking with the cord when there is any rearward tension. Further, the adjustable connector can be a bulbed cord linked to a locking mechanism with interior protrusions or angled surfaces that only allows the bulbed cord to move in a single direction. The adjustable connector can also be a cable tie, or any other mechanism chosen by a skilled artisan that would provide for movement in a single direction.

In operation, the wound closure system works by peeling away or otherwise removing a protective covering from the adhesive backing, and adhering the first main body and the second main body to a patient on opposite sides of a wound. The first and second main bodies are also oriented in a manner that ensures the outer surfaces of the angled walls of the first main body and second main body are facing each other. Once the main bodies are affixed to the patient's skin, the user pulls on the adjustable connector, bringing the first main body and second main body closer together until the wound is closed. Multiple ones of the wound closure system can also be used in series for large lacerations, interspersed in series along a length of the wound.

In another embodiment, the inner surface of the angled wall of the first and second main bodies can face downwards toward the patient's skin. This orientation creates a downward force, helping the main bodies stay attached, while pinching the skin adjacent the wound together.

In a further embodiment, the wound closure system can also contain apertures configured to connect with staples on both the first main body and second main body. This allows the wound closure system to be attached in situations where adhesive is not suitable or usable.

In another embodiment, the wound closure system can have a first main body with fingers and a second main body configured to connect to a plurality of adjustable connectors, referred to as "fingers." Both main bodies can be manufactured for use together in a kit, for example, provided in rolls either separately or temporarily connected, and break off for easy use. The first and second main bodies possess an adhesive backing and a removable adhesive covering. The fingers are affixed to the first main body and selectively couple the first main body to the second main body.

In operation, the adhesive covering is removed and the first and second main bodies are placed on opposite sides of the wound. The first main body is moved toward the second main body by pulling on the fingers until the wound is closed. Once the wound is sealed, the fingers of the first main body are attached to the second main body. The fingers, for example, can attach to the second main body using a hook-and-loop fastener material. The fingers allow the cut to breath while militating against wound separation.

Advantageously, the wound closure system can be used as a stand-alone wound closure device, engaged during the entire duration of the wound heal, or used as a temporary hold on a laceration or operative incision. Multiple wound closure devices may also be used together in series to close lengthy wounds. Moreover, the wound closure system offers surgeons the capability of providing a tension adjustment system during operative suturing or postoperative suturing to assist in resolving complications caused by retention suturing in morbidly obese patients.

DESCRIPTION OF THE DRAWINGS

The above, as well as other advantages of the present invention, will become clear to those skilled in the art from the following detailed description of a preferred embodiment when considered in the light of the accompanying drawings in which.

DETAILED DESCRIPTION

The following detailed description and appended drawings describe and illustrate various exemplary embodiments of the invention. The description and drawings serve to enable one skilled in the art to make and use the invention and are not intended to limit the scope of the invention in any manner. In respect of the methods disclosed, the steps presented are exemplary in nature and, thus, the order of the steps is not necessary or critical.

In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the related drawing. These relative terms are for convenience of description and do not require that the apparatus be constructed or operated in a particular orientation. Terms concerning attachments, such as "connected," "connecting," "coupled," "linked" and "coupling" are used interchangeably and refer to one structure or surface being secured to another structure or surface, unless expressly described otherwise.

Referring to FIGS. 1-8, a wound closure device 2 according to the present disclosure has a first main body 4 and a second main body 6 attached by an adjustable connector 8. The wound closure device 2 is used to securely close a wound of a patient, such as a cut or laceration.

The first main body 4 and the second main body 6 are formed from any rigid or semi-rigid material suitable for medical use. As non-limiting examples, the first main body 4 and the second main body 6 may be formed from a thermoplastic material such as nylon, polyethylene, polypropylene, and the like. Thermoplastics vulcanizates may also be employed. Biodegradable materials, and particularly materials that may be bio-absorbed over time when implanted and after the wound has been sufficiently healed, are also contemplated.

As shown in FIGS. 1-8, each of the first main body 4 and the second main body 6 may have a first portion 17 and a second portion 18. As a non-limiting example, the first portion 17 may be formed from a rigid or semi-rigid thermoplastic material, and the second portion 18 may be formed from a flexible plastic or rubber material, such as a foam rubber material. The first and second portions 18 may be co-molded and physically secured to one another, or may be formed separately and connected by adhesives or mechanical fasteners. One of ordinary skill in the art may select suitable materials and combinations of materials for the first and second main bodies 4, 6 of the wound closure device 2 of the present disclosure, as desired.

The adjustable connector 8 is flexible, to allow for the wound closure device 2 to be used on a wide variety of wounds. As nonlimiting examples, the adjustable connector 8 may be a rope, cord, bulbed cord, or cable tie affixed to a fastener that only allows movement in one direction, for example, as shown in FIGS. 9A-9E and described further hereinbelow. Other suitable types of adjustable connectors 8 may also be employed within the scope of the disclosure, as desired.

Figure 1:
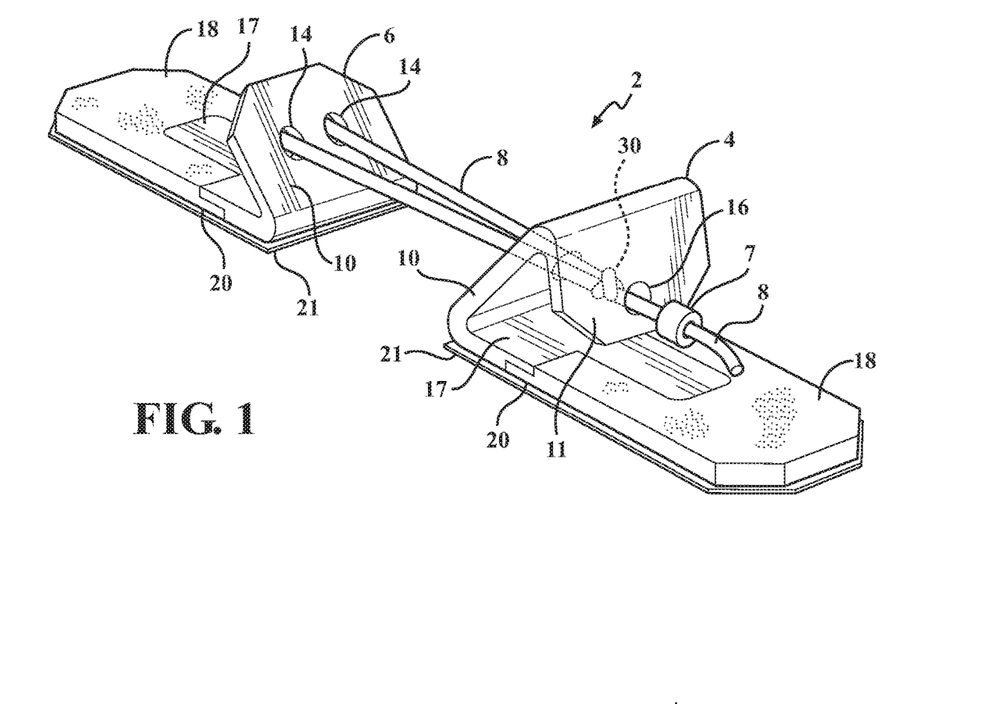
FIG. 1 is a top right perspective view of the wound closure system according to an embodiment of the present disclosure, depicting a single wound closure device with an adhesive backing.
Figure 2:
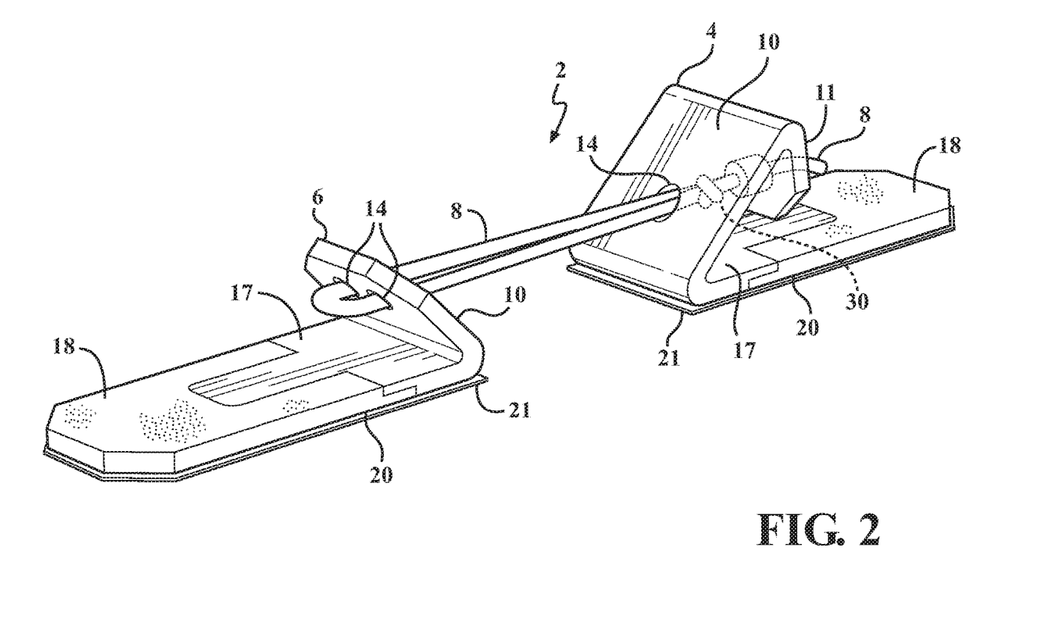
FIG. 2 is a top left perspective view of the wound closure system shown in FIG. 1.
Figure 3:
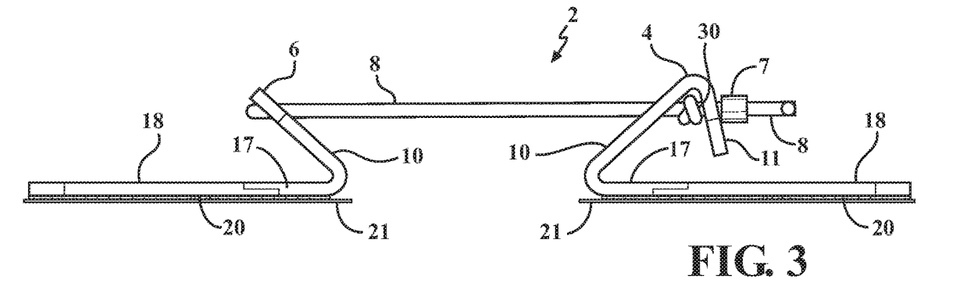
FIG. 3 is a side elevational view of the wound closure system shown in FIG. 1.
Figure 4:
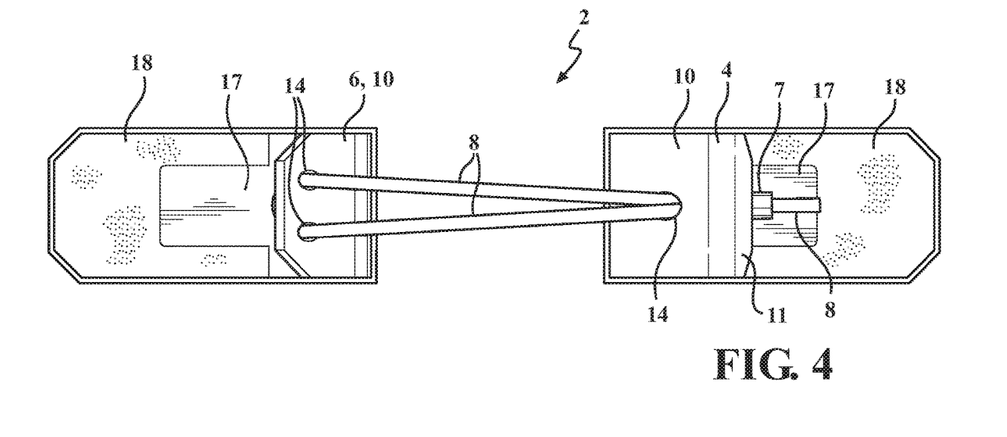
FIG. 4 is a top plan view of the wound closure system shown in FIG. 1.
Figure 5:
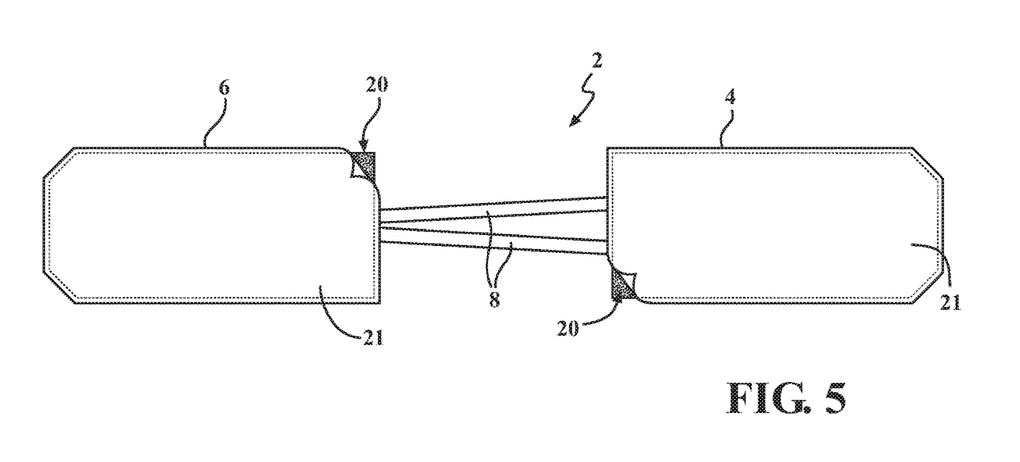
FIG. 5 is a bottom plan view of the wound closure system shown in FIG. 1, with a portion of a removable liner peeled away to show the underlying adhesive.
Figure 6:
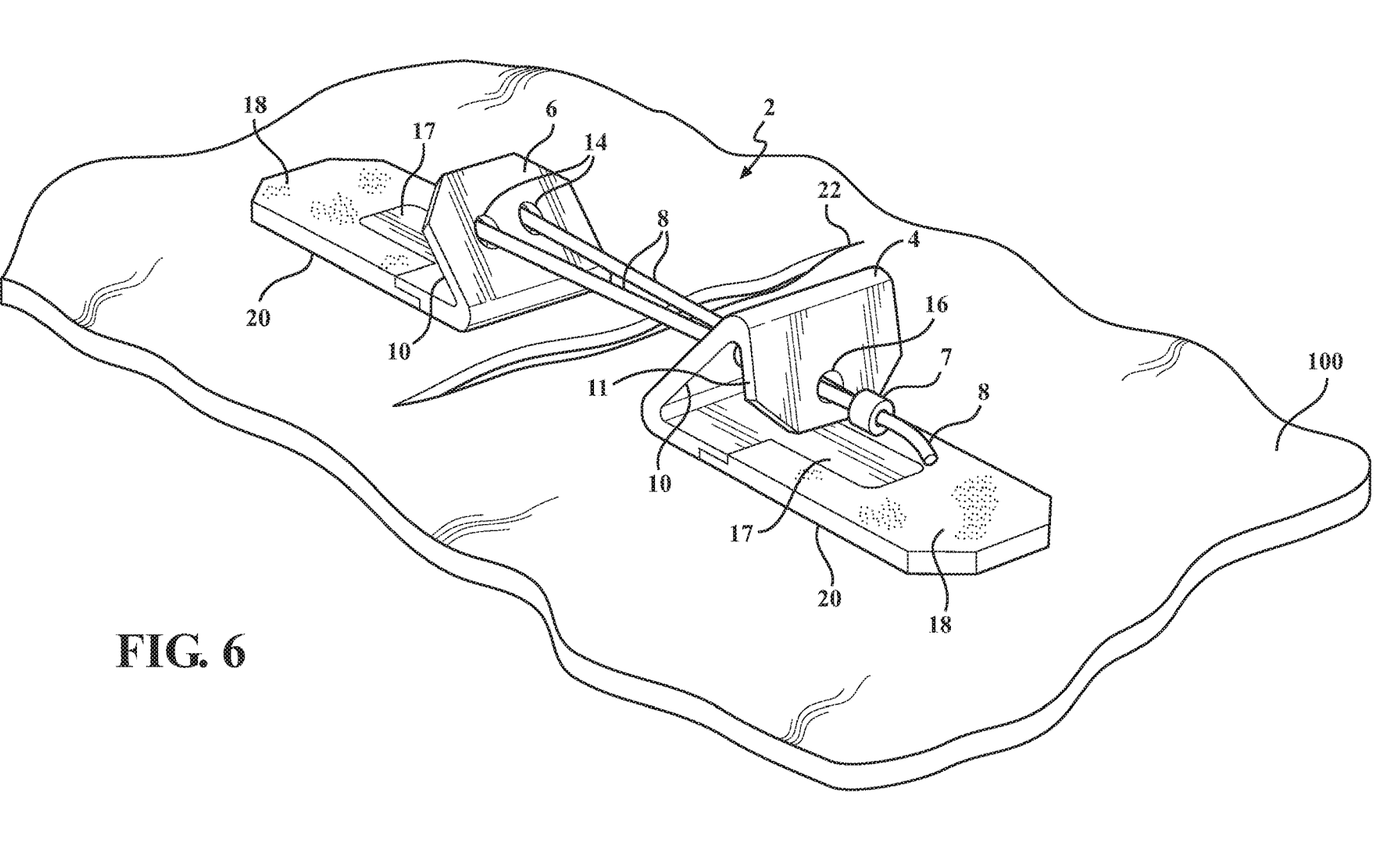
FIG. 6 is a top perspective view of the wound closure system shown in FIG. 1, and further shown attached to skin of a patient over an open wound.
Figure 7:
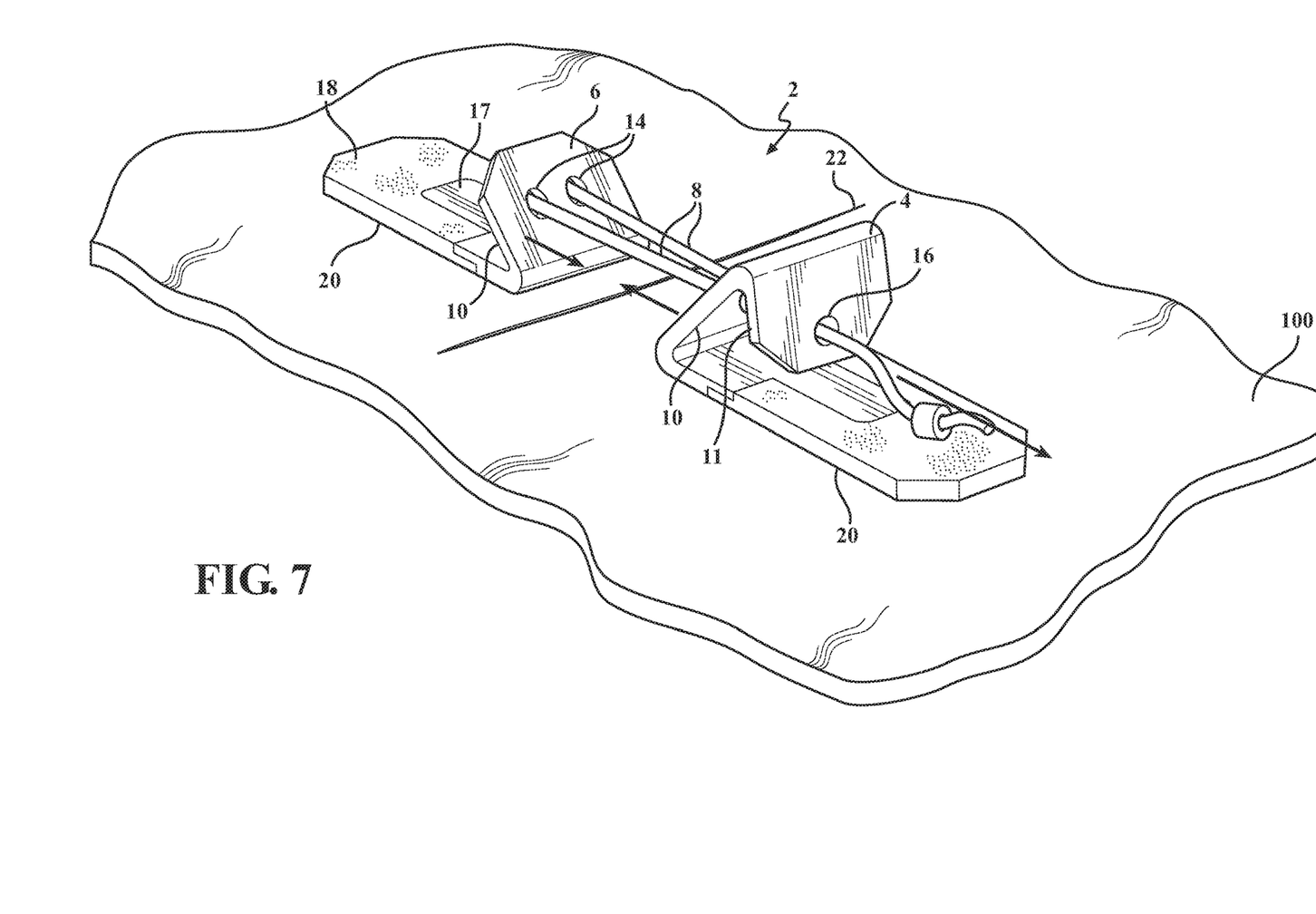
FIG. 7 is a top perspective view of the wound closure system shown in FIG. 1, and further shown attached to skin of a patient over a wound closed by the wound closure device.
Figure 11:
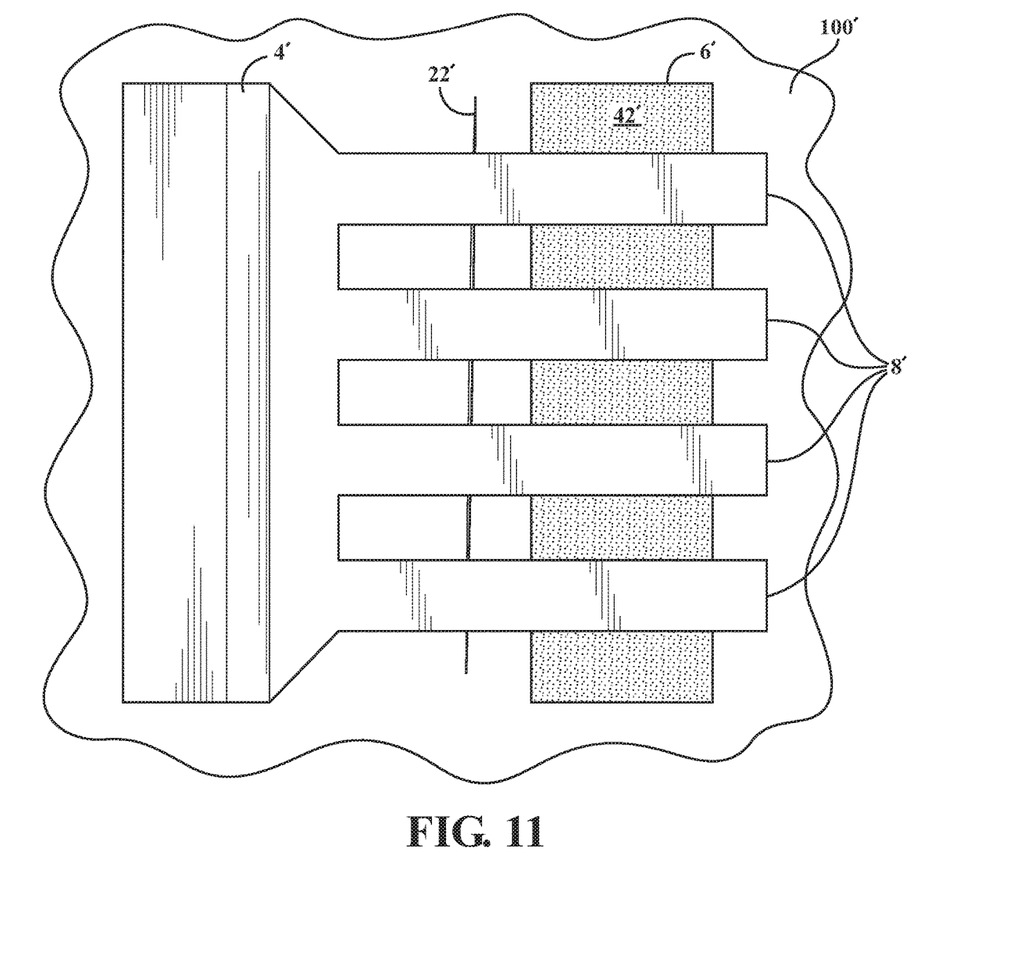
FIG. 11 is a top plan view of the wound closure system shown in FIG. 10, and further shown attached to skin of a patient over a wound closed by the wound closure device.

As shown in FIGS. 1-8, the first main body 4 and the second main body 6 both have an adhesive backing 20 that attach the main bodies 4, 6 to the skin of a patient 100 (shown in FIGS. 6-7 and 11). The adhesive backing 20 may also be selectively covered by a protective covering 21, which can be peeled away from the adhesive backing 20 prior to attachment to the skin of the patient. For example, the adhesive backing may be a type of Cyanoacrylate glue or a medical adhesive tape from 3M such as 3M 1510 3M 1522, 3M 1577, 3M 9832, 3M 9877, 3M 9917, 3M 9880, and 3M 1524, or any other adhesive chosen by a skilled artisan.

With reference to FIG. 6, an adhesive can either be applied directly to the skin, or the protective covering of the adhesive backing 20 may be removed and the first and second main bodies 4, 6 may be placed on the patient's skin on opposite sides of the open wound 22. The adjustable connector 8 is then pulled using a knob, or grasping mechanism 7, in the direction indicated by the arrow shown in FIG.

7. The main bodies 4, 6, which are adhered to the skin, are subsequently drawn closer together in the directions indicated by the arrows shown in FIG. 7 until the wound 22 is closed. Once the wound 22 is closed, a medical professional can further seal the wound using stitches, or a sealant material, as desired.

Additionally, the first and second main bodies 4, 6 can have apertures (not shown) to accommodate staples. Additionally, or in the alternative, the second portion 18 of the first and second main bodies 4, 6 may also be formed from soft and flexible material, such as a foam rubber or the like, which can be pierced by staples. In such cases, the main bodies 4, 6 are placed on opposite sides of a wound and then stapled in place to provide a better grip.

In emergency situations, a patient can be severely bleeding, which might prevent adhesive from binding to the skin. In such situations, the use of staples through the main bodies 4, 6 can enable a medical responder to securely affix the main bodies 4, 6 to the skin. Once the main bodies 4, 6 are affixed to the skin, the cord 8 is pulled using the knob, or grasping mechanism 7, and the main bodies 4, 6 are pulled closer together until the wound 22 is closed. Once the wound 22 is closed, a medical professional can seal the wound 22 using stitches, or a sealant material.

With renewed reference to FIGS. 1-5, the wound closure device 2 according to a particular embodiment of the disclosure may have the first main body 4 and the second main body 6 attached by the adjustable connector 8 in the form of a rope or cord. In this embodiment, the cord 8 is tied in a knot 30 such as a slip knot or uni-slip knot shown in FIGS. 9A and 9B that only allows the cord 8 to only move in one direction. The knot 30 allows the cord 8 to tighten between the two main bodies 4, 6, and prevents the cord from loosening. The first and second main bodies 4, 6 both have the adhesive backing 20 that is removed leaving only the adhesive, which allows the main bodies 4, 6 to attach to the skin.

In this embodiment, the first main body 4 further has an angled housing 12. The angled housing 12 may be defined by an angled wall 10 and a downwardly-extending back portion 11 that results in a substantially triangular- or tent-shaped body that is used to house the knot 30. The second main body 6 also has an angled wall 10. The angled walls 10 of the first and second main bodies 4, 6 serve to direct the force created by tension between the two main bodies downward as the adjustable connector 8 is pulled, thereby providing more grip and surface tension on the skin.

Furthermore, each of the angled walls 10 of the first and second main body 4, 6 contains at least one aperture 14 through which the adjustable connector 8 is disposed. The angle wall of the first main body 4 may have a single aperture 14, which is sized appropriately to allow the adjustable connector 8 to be disposed therethrough while doubled. The angled wall 10 of the second main body 6 may have two apertures 14, for example, which allows the adjustable connector 8 to be looped through the two apertures 14 of the angled wall of 10 of the second main body 6. This looping of the adjustable connector through both apertures 14 of the second main body 6 secures the adjustable connector 8 to the second main body 6.

The downwardly-extending back portion 11 of the angled housing 12 of the first main body 4 may also have a single aperture 16 through which the adjustable connector 8 is likewise disposed. It should be appreciated that only the portion of the adjustable connector 8 that is configured to be gripped and pulled by the user may be disposed through the single aperture 16 of the back portion 11.

Importantly, the single aperture 16 has a diameter that is less than a diameter of the knot 30 contained within the angled housing 12, so that the knot 30 (or a corresponding closure mechanism, described further below) cannot be pulled through the single aperture 16 when the adjustable connector 8 is pulled. In operation, as the adjustable connector 8 is manually pulled, the knot 30 will abut an inner surface of the angled housing 12. This allows the first and second bodies 4, 6, to be irreversibly drawn toward each other as the knot 30 is tightened by the pulling of the adjustable connector 8.

It should be appreciated that the knot 30 shown in FIGS. 1-5 and 9A-9B may be replaced with other types of closure mechanisms that permit the unidirectional travel of the adjustable connector 8 therethrough, and which prevent the cord from retreating therethrough. For example, as shown in FIGS. 9C-9D a closure mechanism 34 may include a boy having a central aperture and a plurality of angled teeth 35. The orientation of the teeth 35 ensure that the adjustable connector 8, such as the cord or closure line, can only be pulled through the central aperture of the closure mechanism 34 in a single direction. When the cord 8 experiences rearward tension, the teeth 35 interlock with the cord 8 stopping it from moving backward. In operation, as the adjustable connector 8 is manually pulled, the closure mechanism 34 will abut the inner surface of the angled housing 12. This allows the first and second bodies 4, 6, to be irreversibly drawn toward each other as the adjustable connector 8 is pulled through the central aperture of the closure mechanism 34 and the single aperture 16 of the angled housing 12.

Figure 9A:
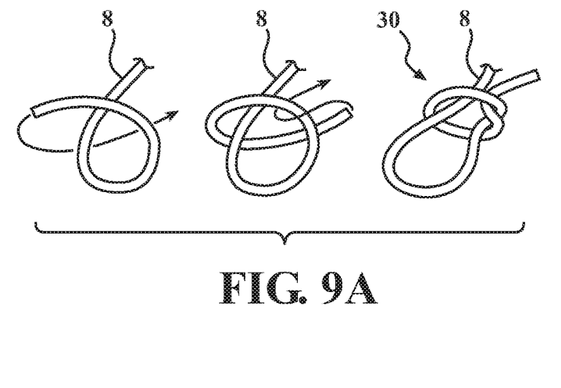
FIG. 9A-9B are partial side elevational views showing slip knots for use with the wound closure system of the present disclosure.
Figure 9B:
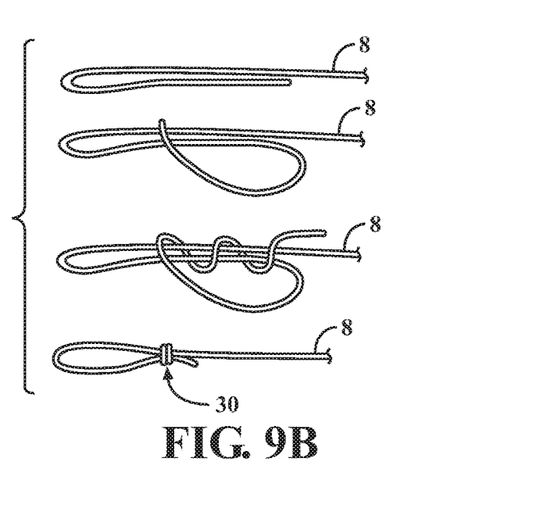
Figure 9C:
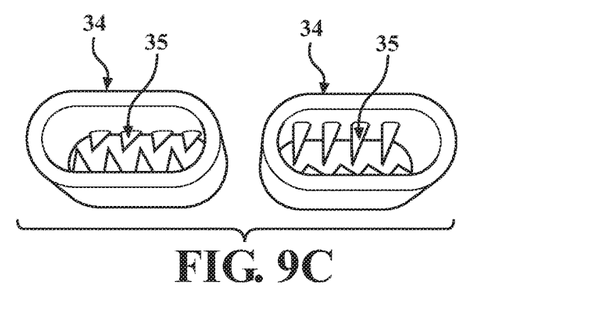
FIGS. 9C-9D are perspective views of closure mechanisms for use with closure lines of the wound closure system of the present disclosure.
Figure 9D:
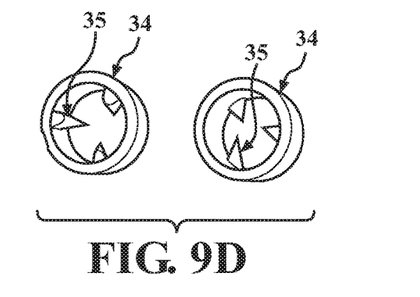
Figure 9E:
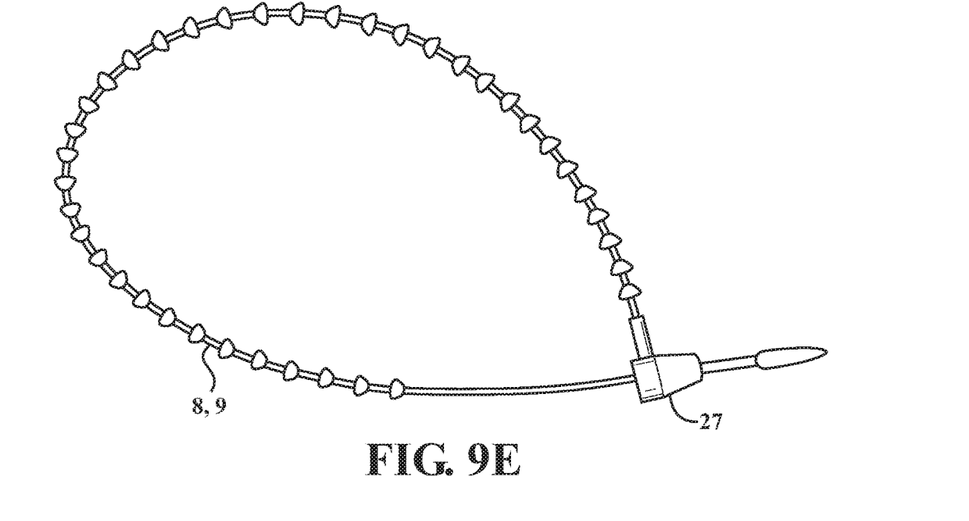
FIG. 9E is a side elevational view showing a beaded closure line for use with the wound closure system of the present disclosure.

In yet another example, the adjustable connector 8 and knot 30 may be replaced with a bulbed cord 9 and locking mechanism 27 as shown in FIG. 9E. The bulbed cord 9 may be affixed to the angled wall 10 on the second main body 6. The angled wall 10 or downwardly-extending back portion 11 on the first main body 4 may be integral with or connected to the one-way locking mechanism 27 that allows the cord to only move in one direction. For example, the locking mechanism 27 may have a set of diagonal flexible protrusions (now shown) that allow the individual bulbs to be pulled forward, but which stop the individual bulbs from moving backwards through the locking mechanism 27. In operation, when the user wishes to apply the wound closure device 2, the adhesive backing 20 is removed and the main bodies 4, 6 are placed adjacent to each other on opposite sides of the wound 22. The bulbed cord 9 is pulled using a knob, or grasping mechanism 7, which results in the main bodies 4, 6 pulling the skin together until the wound 22 is closed. Then the responder can then use stitches, or sealant to bind the wound 22 shut.

Figure 8:
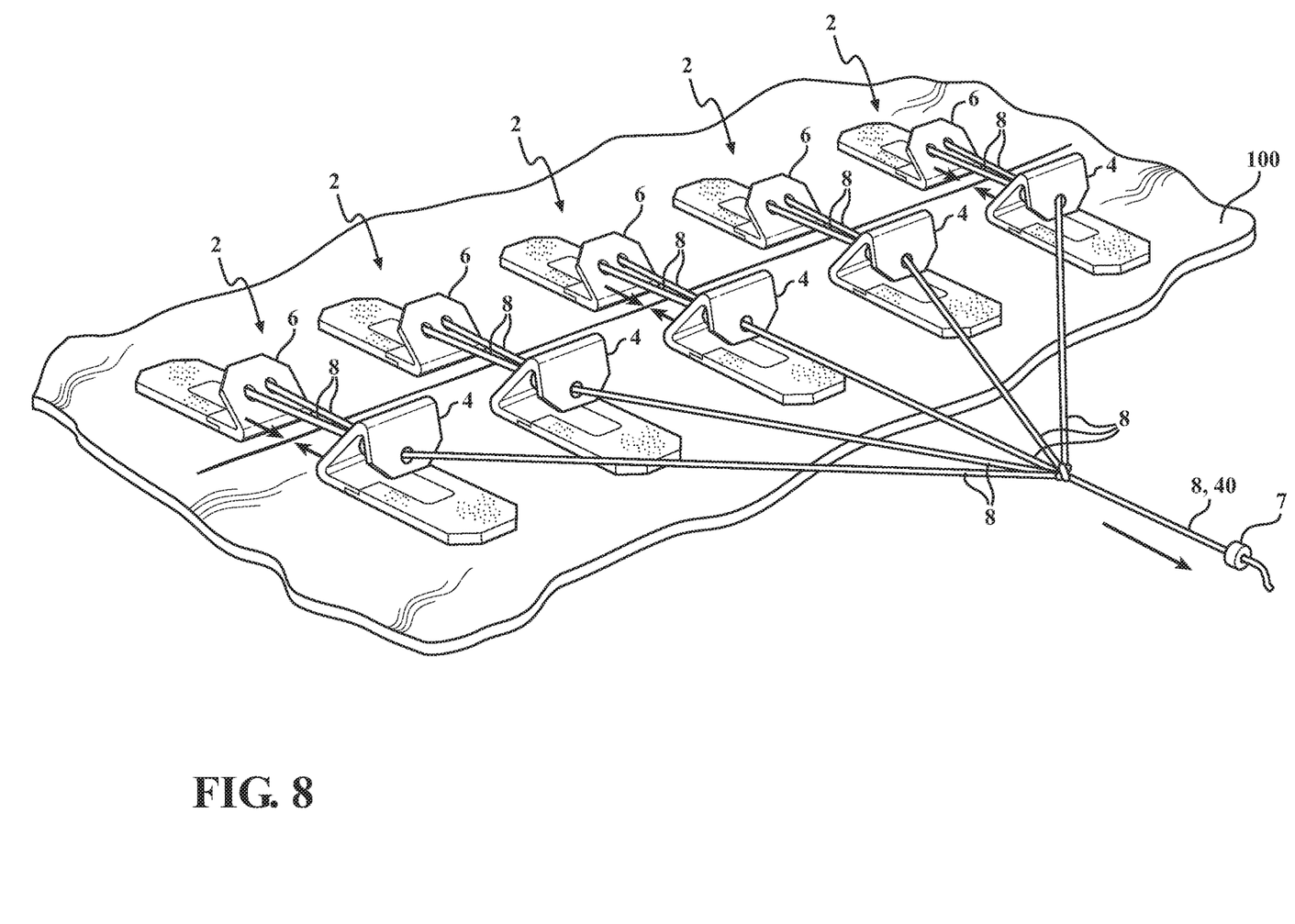
FIG. 8 is a top perspective view of a wound closure system according to another embodiment of the present disclosure including a plurality of the wound closure devices and a singular closure line for operating the wound closure devices simultaneously.

Although the wound closure device 2 is described hereinabove with respect to a single device used to close the wound 22, it should be appreciated that the wound closure device 2 can be used in a series to close larger lacerations 22, as shown in FIG. 38. Multiple wound closure systems 2 are placed with their main bodies 4, 6 on opposite sides of the laceration 22. The adjustable connectors 8 of each of the wound closure systems 2 can be connected to a single pull line 40, for example, to facilitate a simultaneous operation of all of the wound closure along the length of the wound 22. The wound closure systems 2 are then operated to close the laceration 22, as shown in FIG. 8.

FIGS. 9A and 9B illustrate a series of steps to create suitable knot 30 for use with the wound closure device 2 of the disclosure. These knots 30 allow the adjustable connector 8 to move in one direction, while preventing it from moving in the opposite direction. FIG. 9A is a stepwise instruction on how to tie a slip knot, while FIG. 9B is a stepwise instruction on how to tie a uni-slip knot. Other unidirectional knots are also contemplated and within the scope of the present disclosure.

FIGS. 9C and 9D show the closure mechanisms 34 with the teeth 35 that enables adjustable connector 8 to pass one way, but when the adjustable connector 8 is pulled in the opposite direction the teeth 35 interlock with the adjustable connector 8 and secure it in place.

FIG. 9E illustrates an additional embodiment of the wound closure device 2, which has the first main body 4 and the second main body 6 attached by the bulbed cord 9 that allows the main bodies 4, 6 to move closer together while preventing backward motion.

Figure 10:
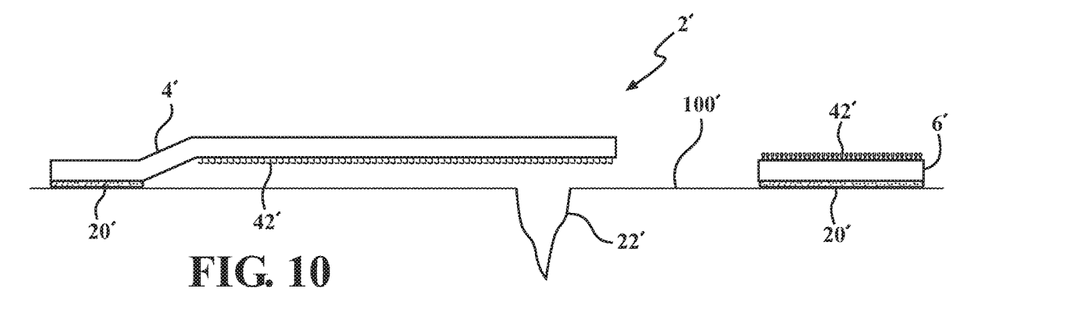
FIG. 10 is a side elevational view of a wound closure system according to yet another embodiment of the present, depicting a wound closure device with an adhesive backing, and fingers connecting the first and second main body.

FIGS. 10 and 11 illustrate a further embodiment of the wound closure device 2' according to the present disclosure. Like or related structure to that shown in FIGS. 1-9E is identified in FIGS. 10 and 11 with the same number and prime symbol (') for purpose of clarity.

As shown in FIG. 10, the wound closure device 2' has a first main body 4' and a second main body 4'. The first main body 4' has a plurality of adjustable connectors or fingers 8' that extend outwardly from the first main body 4' and which are configured to releasably connect or bind with the second main body 6'. Together, the first and second main bodies 4', 6' can be used to close a wound 22', for example, as shown in FIG. 11.

Each of the first and main bodies 4', 6' can be manufactured as a unitary strip of material, rolled into a compact form for distribution and storage, and with individual pieces to be broken off, cut, or torn from the roll for end use. The first and second main bodies 4', 6' have an adhesive backing 20' and a removable protective covering (not shown). In operation, the protective covering is removed and the first and second main bodies 4', 6' are placed on opposite sides of the wound 22', so that the adhesive backing 20' holds the first and second main bodies 4', 6' securely in place on the patient's skin 100'.

The first main body 4' is then moved toward the second main body 6', for example, by pulling on at least one of the fingers 8', until the wound 22' is closed. Once the wound 22' is sealed, the fingers 8' of the first main body 4' are attached to the second main body 6'.

In a particular example, the fingers 8' can attach to the second main body 6' through use of hook-and-loop fastener 42'. The hook-and-loop fastener 42' may be disposed on an underside of the fingers 8' of the first main body 4' and a topside of the second main body 6'. The mating of the hook-and-loop fastener material 42' allows the first main body 4' to be selectively, securely, and reversibly attached to the second main body 6'. The fingers 8' connected by hook-and-loop fastener material also allows the wound 22' to breath while militating against wound separation.

Advantageously, the wound closure device 2, 2' of the present disclosure can be used with minimal training to be securely attached to the patient. The wound closure device 2, 2' is also adjustable, can be rapidly and cleanly applied, and can be used with a wide variety of wound types.

While certain representative embodiments and details have been shown for purposes of illustrating the invention, it will be apparent to those skilled in the art that various changes may be made without departing from the scope of the disclosure, which is further described in the following appended claims.

What is claimed is:

1. A wound closure device comprising:
   a first main body and a second main body, each of the first main body and the second main body having an adhesive backing; and
   an adjustable connector coupling the first main body to the second main body, each of the first main body and the second main body having a first wall, the adjustable connector disposed through the first walls and permitted to be pulled in a single direction to close a wound,
   wherein the first wall of the first main body contains a single aperture configured to receive the adjustable connector,
   wherein the first main body includes a downwardly-extending back portion that depends from the first wall of the first main body,
   wherein the back portion contains a second aperture configured to receive the adjustable connector,
   wherein the front wall and the back portion of the first main body define an angled housing that contains a unidirectional structure of the adjustable connector, the unidirectional structure permitting the adjustable connector to be pulled in only the single direction, and
   wherein one of i) the adjustable connector is a cord and the unidirectional structure is a knot, ii) the adjustable connector is a cord and the unidirectional structure is a closure mechanism including a body having a central hole and angled teeth, and iii) the adjustable connector is a bulbed cord and the unidirectional structure is a body with protrusions that permit bulbs of the bulbed cord to only travel through the body in the single direction.

2. The wound closure device of claim 1, wherein the first wall of the second main body contains two apertures configured to receive the adjustable connector.

3. The wound closure device of claim 1, wherein the knot is a slip knot or a uni-slip knot.

4. The wound closure device of claim 1, wherein the first main body and second main body are configured to receive staples.

5. The wound closure device of claim 1, wherein each of the first main body and the second main body has a first portion and a second portion, the first portion secured to the second portion.

6. The wound closure device of claim 5, wherein the first portion is formed from a rigid or semi-rigid thermoplastic material, and the second portion is formed from a flexible plastic or rubber material.

7. The wound closure device of claim 6, wherein the second portion is formed from foam rubber.

8. A wound closure system, comprising a plurality of the wound closure devices of claim 1 arranged in a series along a length of the wound.

9. The system of claim 8, further comprising a single closure or pull line connected to each of the adjustable connectors for operating the wound closure devices simultaneously.

10. A method for closing a wound, the method comprising steps of:
    providing a wound closure device including a first main body and a second main body, each of the first main body and the second main body having an adhesive backing, and an adjustable connector coupling the first main body to the second main body, each of the first main body and the second main body having a first wall, the adjustable connector disposed through the first walls and permitted to be pulled in a single direction, wherein the first wall of the first main body contains a single aperture configured to receive the adjustable connector, wherein the first main body includes a downwardly-extending back portion that depends from the first wall of the first main body, wherein the back portion contains a second aperture configured to receive the adjustable connector, wherein the front wall and the back portion of the first main body define an angled housing that contains a unidirectional structure of the adjustable connector, the unidirectional structure permitting the adjustable connector to be pulled in only the single direction, and wherein one of i) the adjustable connector is a cord and the unidirectional structure is a knot, ii) the adjustable connector is a cord and the unidirectional structure is a closure mechanism including a body having a central hole and angled teeth, and iii) the adjustable connector is a bulbed cord and the unidirectional structure is a body with protrusions that permit bulbs of the bulbed cord to only travel through the body in the single direction;

applying the first main body and the second main body to a patient on opposite sides of the wound, ensuring the first walls of the first main body and second main body are facing each other; and pulling the adjustable connector on the first main body, thereby tightening the adjustable connector and pulling the first main body and second main body closer together until the wound is closed.

11. The method of claim 10, further comprising a plurality of the wound closure devices arranged in a series along a length of the wound, and the pulling of the adjustable connectors includes a pulling of single closure or pull line connected to each of the adjustable connectors.

* * * * *